United States Patent
Rhodes et al.

(10) Patent No.: US 10,692,594 B2
(45) Date of Patent: Jun. 23, 2020

(54) METHODS FOR IMPROVING NATURAL LANGUAGE PROCESSING WITH ENHANCED AUTOMATED SCREENING FOR AUTOMATED GENERATION OF A CLINICAL SUMMARIZATION REPORT AND DEVICES THEREOF

(71) Applicant: eHealth Technologies, West Henrietta, NY (US)

(72) Inventors: Colin Rhodes, Rochester, NY (US); Chad Malone, Pittsford, NY (US); Ken Rosenfeld, Pittsford, NY (US)

(73) Assignee: EHEALTH TECHNOLOGIES, West Henrietta, NY (US)

( * ) Notice: Subject to any disclaimer, the term of this patent is extended or adjusted under 35 U.S.C. 154(b) by 223 days.

(21) Appl. No.: 15/584,764

(22) Filed: May 2, 2017

(65) Prior Publication Data
US 2018/0322110 A1    Nov. 8, 2018

(51) Int. Cl.
*G06F 17/27* (2006.01)
*G16H 10/60* (2018.01)
(Continued)

(52) U.S. Cl.
CPC .......... *G16H 10/60* (2018.01); *G06F 16/3344* (2019.01); *G06F 40/186* (2020.01);
(Continued)

(58) Field of Classification Search
CPC ....................................................... G06F 17/27
(Continued)

(56) References Cited

U.S. PATENT DOCUMENTS 5,963,205 A * 10/1999 Sotomayor ........... G06F 40/137
715/236
6,766,287 B1 * 7/2004 Kupiec ................. G06F 40/253
704/9

(Continued)

OTHER PUBLICATIONS

"Eligible Professional Meaningful Use Core Measures, Measure 12 of 13, Stage 1", May 2014, 3 pages, [retrieved on May 2, 2017]. Retrieved from the Internet: <https://www.cms.gov/Regulations-and-Guidance/Legislation/EHRIncentivePrograms/downloads/13_Clinical_Summaries.pdf.>.

(Continued)

*Primary Examiner* — Michael Colucci
(74) *Attorney, Agent, or Firm* — Pepper Hamilton LLP

(57) ABSTRACT

Methods, non-transitory computer readable media, and devices that convert into a common electronic format a plurality electronic medical records retrieved in response to a request with identification data. A natural language processing algorithm is applied to obtain a subset of summarization data from each of the converted medical electronic record based on medical information data in the received request. The algorithm screens the initial subset of summarization data based on one or more factors to generate a reduced subset of summarization data for each of the converted medical electronic records. At least a portion of the reduced subset of summarization data is populated into data fields within one of a plurality of templates identified for each of the converted electronic medical records from the reduced subset of summarization data. A clinical summarization record is generated based on at least the populated summarization data in each of the identified ones of the plurality of templates. The clinical summarization record is provided in response to the received request.

21 Claims, 4 Drawing Sheets

(51) Int. Cl.
*G16H 15/00* (2018.01)
*G06F 16/33* (2019.01)
*G06F 40/186* (2020.01)
*G06F 40/258* (2020.01)
*G06F 40/279* (2020.01)

(52) U.S. Cl.
CPC .......... *G06F 40/258* (2020.01); *G06F 40/279* (2020.01); *G16H 15/00* (2018.01)

(58) Field of Classification Search
USPC ............ 704/235, 9, 270, 270.1, 275, 2, 234; 345/467; 379/88.04, 218.01; 715/254, 715/242, 236, 781
See application file for complete search history.

(56) References Cited

U.S. PATENT DOCUMENTS

| | | | | |
|---|---|---|---|---|
| 7,206,389 | B1* | 4/2007 | Dumoulin | G10L 15/1822 379/218.01 |
| 8,065,151 | B1* | 11/2011 | Bangalore | G10L 15/22 704/270 |
| 10,360,301 | B2* | 7/2019 | Allen | G06F 40/242 |
| 2004/0243545 | A1* | 12/2004 | Boone | G06F 19/00 |
| 2006/0080140 | A1* | 4/2006 | Buttner | G06Q 10/10 705/2 |
| 2007/0219986 | A1* | 9/2007 | Egozi | G06F 16/313 |
| 2008/0133516 | A1* | 6/2008 | Itzhak | G06F 16/9535 |
| 2010/0049498 | A1* | 2/2010 | Cao | G06F 40/284 704/9 |
| 2011/0184718 | A1* | 7/2011 | Chen | G06F 40/253 704/2 |
| 2013/0021346 | A1* | 1/2013 | Terman | G09B 5/08 345/467 |
| 2013/0144607 | A1* | 6/2013 | Weber | G10H 1/46 704/9 |
| 2013/0332467 | A1* | 12/2013 | Bornea | G06F 16/951 707/747 |
| 2015/0095770 | A1* | 4/2015 | Mani | G06F 16/345 715/254 |
| 2015/0317285 | A1* | 11/2015 | Duggal | G06F 16/345 715/242 |
| 2018/0032608 | A1* | 2/2018 | Wu | G06F 16/345 |
| 2018/0075011 | A1* | 3/2018 | Allen | G16H 50/50 |
| 2019/0114298 | A1* | 4/2019 | Acharya | G06F 16/3334 |

OTHER PUBLICATIONS

Feblowitz et al., "Summarization of Clinical Information: A Conceptual Model", Journal of Biomedical Informatics, Aug. 2011, pp. 688-699, vol. 44, Issue 4, Elsevier Inc.

Korde et al., "Text Classification and Classifiers: A Survey", International Journal of Artificial Intelligence & Applications (IJAIA), Mar. 2012, pp. 85-99, vol. 3, No. 2, Sardar Vallabhbhai National Institute of Technology, Surat.

Lee, "The Use of Bigrams to Enhance Text Categorization", Jul. 2002, pp. 1-31, vol. 38, No. 4, Technical, Department of Computer Science, University of California, CA.

Pevnick et al., "The Problem With Medication Reconciliation", Dec. 1, 2015, pp. 1-6, BMJ Publishing Group Ltd.

Pivovarov et al., "Automated Methods for the Summarization of Electronic Health Records", Oct. 30, 2014, pp. 938-947, vol. 22, No. 5, Med Inform Assoc., AMIA, Oxford University Press.

Sebastiani, "Machine Learning in Automated Text Categorization", 2002, p. 1-47, vol. 34, No. 1, ACM Computing Surveys (CSUR) (ACM).

* cited by examiner

182641 Rhodes, Colin

| Rhodes, Colin | | | 12/3/1970 | | 182641 |
| --- | --- | --- | --- | --- | --- |
| Diagnosis: METASTATIC ADENOCARCINOMA | | | | | |

| Date | Document Type | By Author | Specialty | Facility |
| --- | --- | --- | --- | --- |
| 9/8/2015 | Radiology | MORRIS TOD A | Oncology | NAVAL MEDICAL CENTER PORTSMOUTH |

SubType: MRI with Contrast      Body Part: Brain

Indications: History of lung cancer with metastatic disease to the brain. Patient is currently receiving chemotherapy of Pemetrexed and Avastin. Patient will nee MRI of brain prior to next cycle of chemotherapy.

Findings: Again demonstrated are multiple foci of susceptibility artifact in the left cerebellar hemisphere, the right parietal, left parieto-occipital and bilateral occipital lobes, intervally unchanged. No new foci of susceptibility artifact are appreciated. Within the right cerebellar hemisphere, there is a rounded focus of T2/FLAIR hyperintensity that enhances on postcontrast sequences, without significant interval change in size or appearance. There are no new regions of abnormal postcontrast enhancement or signal intensity in the brain parenchyma. There is no mass effect or midline shift. There is no evidence of acute hemorrhage or infarction. No areas of restricted diffusion are present. There are no areas 0 abnormal contrast enhancement involving the pachymeninges or leptomeninges. The midline structures and posterior fossa are normally formed. The ventricles and cisterns are normal in size. There are no abnormal extra-axial fluid collections. The soft tissue structures including the orbits, pharynx and paranasal sinuses are unremarkable. Normal flow voids are present within the visualized major vessels. There are no marrow replacing osseous lesions.

Impressions: No evidence of new metastatic disease. The previously identified right cerebellar hemisphere metastatic lesion is intervally unchanged.

| Date | Document Type | By Author | Specialty | Facility |
| --- | --- | --- | --- | --- |
| 10/6/2014 | Pathology | ABAIS,PETER D | Allergy/Immunology | NMC PORTSMOUTH |

SubType: Cytopathology      Body Part: Chest

Diagnosis: PLEURAL FLUID (CYTOLOGY). - SATISFACTORY FOR EVALUATION. - MALIGNANT CELLS PRESENT CONSISTENT WITH METASTATIC ADENOCARCINOMA, LUNG PRIMARY (SEE COMMENT). COMMENT: Immunohistochemical studies reveal strong immunoreactivity for TIF-1 (nuclear) and CK7 (cytoplasmic and membranous). B72.3 (TAG72) is non-contributory.

Gross Description: RECEIVED GREATER THAN 100 MLS OF YELLOW / BROWN FLUID.

| Date | Document Type | By Author | Specialty | Facility |
| --- | --- | --- | --- | --- |
| 10/5/2014 | H&P, Consults, Office/Progress Notes | STRANGE ROBERT GEORGE | Allergy/Immunology | NMC PORTSMOUTH |
| 9/15/2014 | H&P, Consults, Office/Progress Notes | ORI TIMOTRY R | Allergy/Immunology | LANGLEY |

FIG. 4

METHODS FOR IMPROVING NATURAL LANGUAGE PROCESSING WITH ENHANCED AUTOMATED SCREENING FOR AUTOMATED GENERATION OF A CLINICAL SUMMARIZATION REPORT AND DEVICES THEREOF

FIELD

This invention relates to methods for improving natural language processing with enhanced automated screening for automated generation of a clinical summarization report and devices thereof.

BACKGROUND

Clinical summarization is the act of collecting, distilling, and synthesizing patient information for the purpose of facilitating any of a wide range of clinical tasks. Four categories of clinical summaries are defined as: Extractive Summaries which are created by borrowing unaltered text; Abstract Summaries which generate new text based upon synthesis and each category can be extended by a further dimension; Indicative Summaries which point to important parts of the text to provide highlights of significant information; and Informative Summaries which replace the patient record and can be used as a replacement of all the original data.

Prior approaches to generate a clinical summary have typically relied on nurses in the hospital working through the entire record set manually and copying relevant data into an excel spreadsheet. This clinical summarization is then presented to the physician for review during the first patient appointment. Unfortunately, this process of generating these prior clinical summarizations is inefficient, time consuming, and often may miss relevant data negatively impacting patient care.

Additionally, in other non-medical related fields natural language processing algorithms have been used to process and analyze text. Although helpful these natural language processing algorithms have had computer processing issues in accurately and effectively processing and understanding complicated text. As a result, when these prior natural language processing algorithms have been applied, inferior results are often obtained.

SUMMARY

A method for improving natural language processing with enhanced automated screening for automated generation of a clinical summarization report implemented by a clinical summary management computing system comprising one or more clinical summary management computing apparatuses, client devices, or server devices includes converting into a common electronic format a plurality of different types of electronic medical records retrieved in response to a received request with patient identification data. A natural language processing algorithm is applied to obtain a subset of summarization data from each of the converted medical electronic records based on medical information data in the received request. The natural language processing algorithm also screens the initial subset of summarization data based on one or more factors to generate a reduced subset of summarization data for each of the converted medical electronic records. At least a portion of the reduced subset of summarization data is populated into a plurality of data fields within one of a plurality of templates identified for each of the converted electronic medical records from the reduced subset of summarization data for each of the converted medical electronic records. A clinical summarization record is generated based on at least the populated summarization data in each of the identified ones of the plurality of templates. The clinical summarization record is provided in response to the received request.

An electronic medical records computing apparatus, comprising memory comprising programmed instructions stored thereon and one or more processors configured to be capable of executing the stored programmed instructions to convert into a common electronic format a plurality of different types of electronic medical records retrieved in response to a received request with patient identification data. A natural language processing algorithm is applied to obtain a subset of summarization data from each of the converted medical electronic records based on medical information data in the received request. The natural language processing algorithm also screens the initial subset of summarization data based on one or more factors to generate a reduced subset of summarization data for each of the converted medical electronic records. At least a portion of the reduced subset of summarization data is populated into a plurality of data fields within one of a plurality of templates identified for each of the converted electronic medical records from the reduced subset of summarization data for each of the converted medical electronic records. A clinical summarization record is generated based on at least the populated summarization data in each of the identified ones of the plurality of templates. The clinical summarization record is provided in response to the received request.

A non-transitory computer readable medium having stored thereon instructions for improving natural language processing with enhanced automated screening for automated generation of a clinical summarization report comprising executable code which when executed by one or more processors, causes the one or more processors to convert into a common electronic format a plurality of different types of electronic medical records retrieved in response to a received request with patient identification data. A natural language processing algorithm is applied to obtain a subset of summarization data from each of the converted medical electronic records based on medical information data in the received request. The natural language processing algorithm also screens the initial subset of summarization data based on one or more factors to generate a reduced subset of summarization data for each of the converted medical electronic records. At least a portion of the reduced subset of summarization data is populated into a plurality of data fields within one of a plurality of templates identified for each of the converted electronic medical records from the reduced subset of summarization data for each of the converted medical electronic records. A clinical summarization record is generated based on at least the populated summarization data in each of the identified ones of the plurality of templates. The clinical summarization record is provided in response to the received request.

This technology provides a number of advantages including providing methods, non-transitory computer readable media, and devices for improving natural language processing with enhanced automated screening for automated generation of a clinical summarization report. Examples of this technology achieve a higher level of accuracy through the use of a natural language processing (NLP) algorithm with enhanced automated screening that more accurately obtains and screens key concepts and provides automated guidance on summarization data to be included in the clinical summarization report. As a result, this technology substantially reduces the possibility of overlooking important retrieved data that may be contained within large records of data while also further increasing efficiency. Additionally, examples of this technology provide substantially more accurate clinical summarization reports through the use of an automated template-based system that is specific to and may be selected based on factors, such as an automated identification of diagnosis codes, and/or disease type.

BRIEF DESCRIPTION OF THE DRAWINGS

FIG. 4 is an example of a generated clinical summarization report.

DETAILED DESCRIPTION

Figure 1:
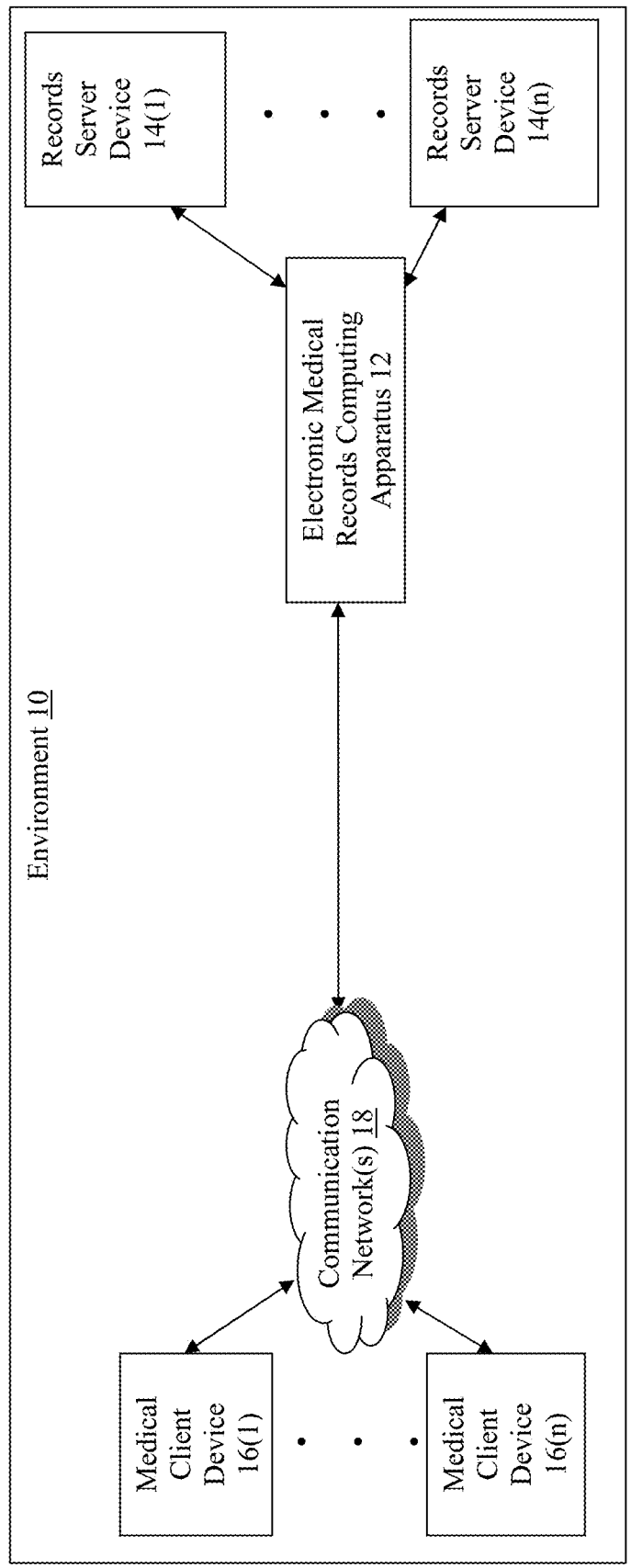
FIG. 1 is a diagram of a network environment with an example of a clinical summary management computing apparatus.

Referring to FIG. 1, an exemplary network environment 10 which incorporates an exemplary electronic medical records computing apparatus 12 is illustrated. In this particular example, the electronic medical records computing apparatus 12 is coupled to a plurality of records server devices 14(1)-14(n) and a plurality of medical client devices 16(1)-16(n) via communication network(s) 18, although the electronic medical records computing apparatus 12, records server devices 14(1)-14(n), and/or medical client devices 16(1)-16(n) may be coupled together via other topologies. Additionally, the electronic medical records computing apparatus 12 may include other network devices such as one or more routers and/or switches, for example, which are well known in the art and thus will not be described herein. This technology provides a number of advantages including methods, non-transitory computer readable media, and clinical summary management computing apparatuses that optimize natural language processing with enhanced automated screening for automated generation of a clinical summarization report.

Figure 2:
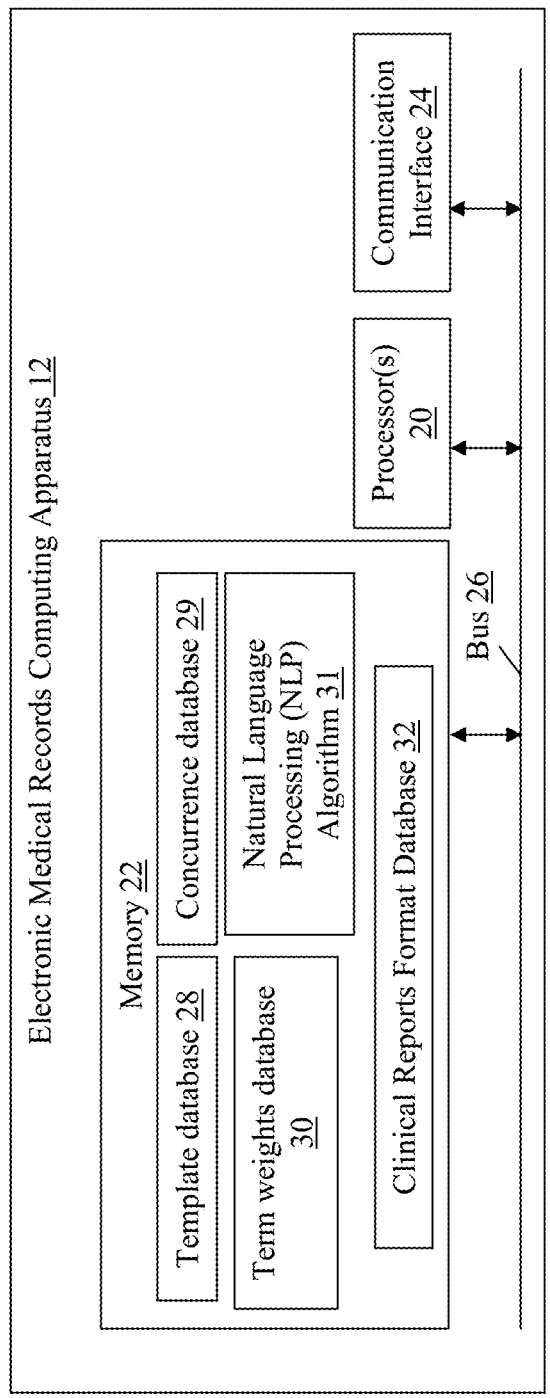
FIG. 2 is a block diagram of an example of the clinical summary management computing apparatus.

Referring to FIGS. 1-2, the electronic medical records computing apparatus 12 may perform any number of functions including improving natural language processing with enhanced automated screening for automated generation of a clinical summarization report. The electronic medical records computing apparatus 12 includes one or more processors 20, a memory 22, and/or a communication interface 24, which are coupled together by a bus or other communication link 26, although the electronic medical records computing apparatus 12 can include other types and/or numbers of elements in other configurations.

The processor(s) 20 of the electronic medical records computing apparatus 12 may execute programmed instructions stored in the memory 22 of the electronic medical records computing apparatus 12 for the any number of the functions illustrated and described by way of the examples herein. The processor(s) 20 of the electronic medical records computing apparatus 12 may include one or more CPUs or general purpose processors with one or more processing cores, for example, although other types of processor(s) can also be used.

The memory 22 of the electronic medical records computing apparatus 12 stores these programmed instructions for one or more aspects of the present technology as described and illustrated by way of the examples herein, although some or all of the programmed instructions could be stored elsewhere. A variety of different types of memory storage devices, such as random access memory (RAM), read only memory (ROM), hard disk, solid state drives, flash memory, or other computer readable medium which is read from and written to by a magnetic, optical, or other reading and writing system that is coupled to the processor(s), can be used for the memory 22.

Figure 3:
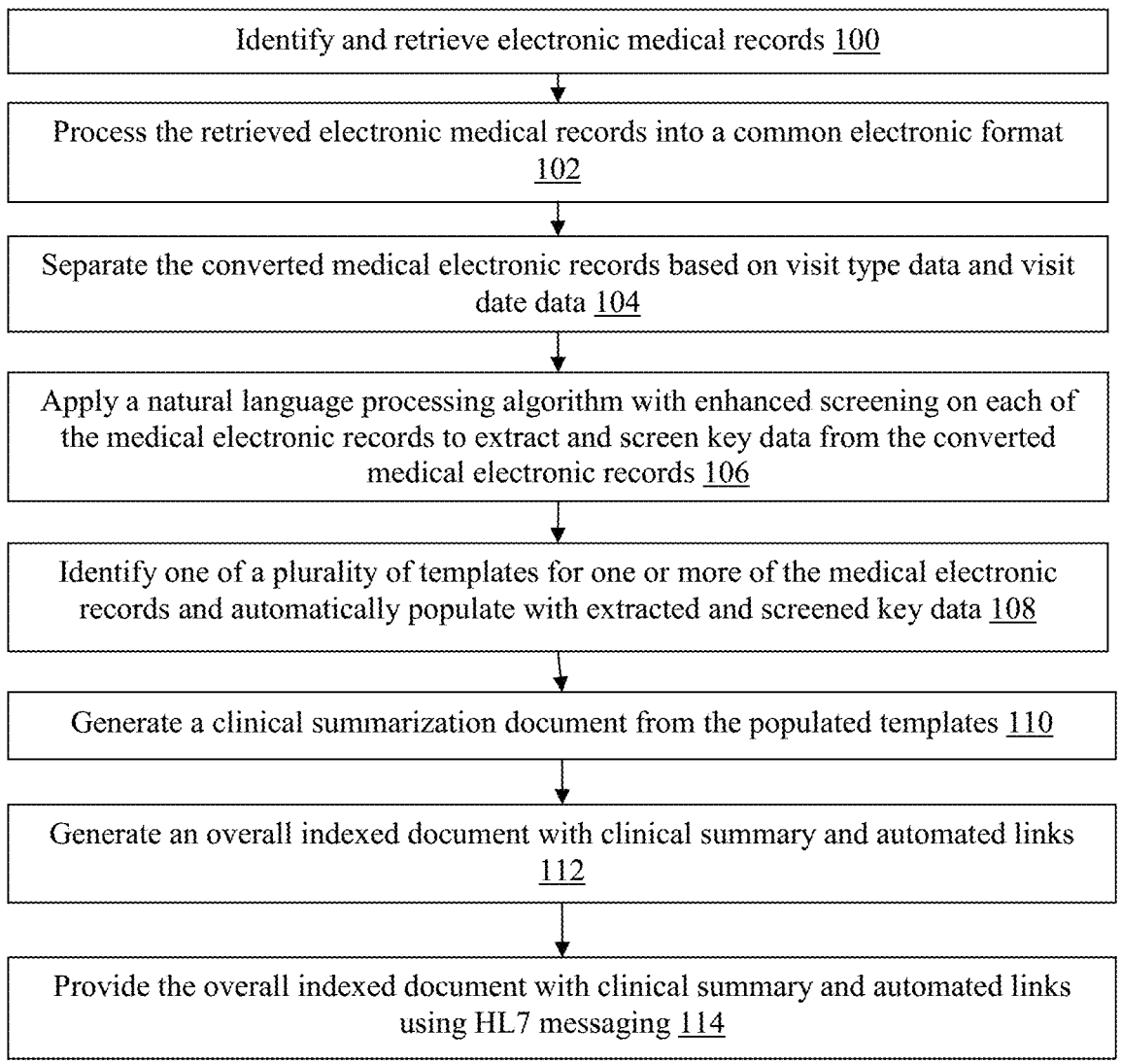
FIG. 3 is a flow chart of an example of a method for improving natural language processing with enhanced automated screening for automated generation of a clinical summarization report.

Accordingly, the memory 22 of the electronic medical records computing apparatus 12 can store one or more applications that can include computer executable instructions that, when executed by the electronic medical records computing apparatus 12, cause the electronic medical records computing apparatus 12 to perform actions, such as to perform actions as described and illustrated in the examples below with reference to FIGS. 3-4. The application(s) can be implemented as modules or components of other applications. Further, the application(s) can be implemented as operating system extensions, module, plugins, or the like.

Even further, the application(s) may be operative in a cloud-based computing environment. The application(s) can be executed within or as virtual machine(s) or virtual server(s) that may be managed in a cloud-based computing environment. Also, the application(s), and even the electronic medical records computing apparatus 12 itself, may be located in virtual server(s) running in a cloud-based computing environment rather than being tied to one or more specific physical network computing devices. Also, the application(s) may be running in one or more virtual machines (VMs) executing on the electronic medical records computing apparatus 12. Additionally, in one or more embodiments of this technology, virtual machine(s) running on the electronic medical records computing apparatus 12 may be managed or supervised by a hypervisor.

In this particular example, the memory 22 of the electronic medical records computing apparatus 12 includes a template database 28, a concurrence database 29, a term weights database 30, a natural language processing (NLP) algorithm 31, and a clinical reports format database 32, although the memory can include other types and/or numbers of other policies, modules, databases, or applications, for example. The template database 28 may comprise a plurality of stored templates which are organized based on an associated institution, department and/or disease type, although other types and/or numbers of templates which are stored in other manners may be used. The concurrence database 29 may comprise a plurality of stored relationships between terms, such as different medical terms which may be within the same field or associated with a particular disease or condition by way of example only, whose concurrence within a document may be utilized in screening during natural language processing, although other types and/or numbers of concurrences which are stored in other manners may be used. The term weights database 30 may comprise a plurality of stored weights for particular terms, such as different weights applied to different medical terms by way of example only, although other types and/or numbers of weights or other screening adjustments may be used The natural language processing (NLP) algorithm 31 is a software program that automates translation between computer and retrieved text of human languages and uses enhanced automated screening as illustrated and described by way of the examples herein, although other types and/or numbers of record processing algorithms could be used. The NLP algorithm 31 can for example locate "findings" and "impressions" sections within a radiology visit file medical record using the enhanced screening so that the identified data can be used to populate relevant data fields within an identified template. In another example of the enhanced automated screening, the execution of the NLP algorithm 31 can also obtain a diverse set of "named entities" from within each section, and then may use the concurrence database 29 and/or the term weights database 30 along with for example one or more other factors, such as the frequency of one or more terms within a document, to reduce the initially identified terms to a more manageable and accurate subset for generating a clinical summarization. The NLP algorithm 31 with the enhanced automated screening also can be used to guide the eye of a clinical professional using one of the medical client devices 16(1)-16(n) to particular key terms in an electronic medical record based on the enhanced automated screening, such as particular types of "named entities" within a visit file record. For example, the electronic medical records computing apparatus 12 executing the NLP algorithm 31 may highlight the term "congestive heart failure" in a retrieved electronic medical record to alert the clinical professional using one of the medical client devices 16(1)-16(n) to the presence of this disease and who can then, using one of the medical client devices 16(1)-16(n), make a determination on whether to include this in the template based on their clinical judgement. Further, the clinical professional interacting with the electronic medical records computing apparatus 12 may click on with the mouse button or otherwise select a term displayed during and/or following the execution of the NLP algorithm 31 to update the weight in the term weights database 30, such as a term related to a current disease state, thus increasing or decreasing the selected term's relative importance for the current or future enhanced screenings by the NLP algorithm 31. The clinical reports format database 32 may comprise a plurality of stored clinical summarization report formats which are based on the particular institution associated with the received request, although other types and/or numbers of clinical summarization report formats which are stored in other manners may be used.

By way of a further example, when presented with a long passage of text within a converted visit file medical electronic record, the execution of the NLP algorithm 31 identifies one or more relevant sections within that converted medical electronic record. An example of this may be for example the "findings" and "impressions" sections within a radiology note that in this example is one of the converted medical electronic records that was retrieved. In the converted electronic medical record, terms matching for example stored terms are identified within each section, resulting in the identification of for example lymph node status, presence of metastatic disease, and so forth. Additionally, each of the identified terms may have a different relative importance in the context of the disease state under examination which is reflected by a different stored weight for each of terms. If a particular term's weight is greater than a given threshold, then the identified term and any surrounding context sentences for an adjustably stored range may be for example included in the clinical summarization report output. This weight-based filter allows the section text to be "pared down" to a shorter, more condensed format that can subsequently be automatically transferred to a mapped location in an identified clinical template and may be further verified for correctness by a clinical professional.

The communication interface 24 of the electronic medical records computing apparatus 12 operatively couples and communicates between the electronic medical records computing apparatus 12, the records server devices 14(1)-14(n), and/or the medical client devices 16(1)-16(n), which are all coupled together by the communication network(s) 18, although other types and/or numbers of communication networks or systems with other types and/or numbers of connections and/or configurations to other devices and/or elements can also be used.

By way of example only, the communication network(s) 18 can include local area network(s) (LAN(s)) or wide area network(s) (WAN(s)), and can use TCP/IP over Ethernet and industry-standard protocols, although other types and/or numbers of protocols and/or communication networks can be used. The communication network(s) in this example can employ any suitable interface mechanisms and network communication technologies including, for example, tele-traffic in any suitable form (e.g., voice, modem, and the like), Public Switched Telephone Network (PSTNs), Ethernet-based Packet Data Networks (PDNs), combinations thereof, and the like. The communication network(s) 18 can also include one or more direct connection(s) (e.g., for when a device illustrated in FIG. 1, such as the electronic medical records computing apparatus 12, one or more of the medical client devices 16(1)-16(n), or one or more of the records server devices 14(1)-14(n) operate as virtual instances on the same physical machine).

While the electronic medical records computing apparatus 12 is illustrated in this example as including a single device, the electronic medical records computing apparatus 12 in other examples can include a plurality of devices or blades each having one or more processors (each processor with one or more processing cores) that implement one or more steps of this technology. In these examples, one or more of the devices can have a dedicated communication interface or memory. Alternatively, one or more of the devices can utilize the memory, communication interface, or other hardware or software components of one or more other devices included in the electronic medical records computing apparatus 12.

Additionally, one or more of the devices that together comprise the electronic medical records computing apparatus 12 in other examples can be standalone devices or integrated with one or more other devices or apparatuses, such as one of the records server devices 14(1)-14(n) or one of the medical client devices 16(1)-16(n), for example. Moreover, one or more of the devices of the electronic medical records computing apparatus 12 in these examples can be in a same or a different communication network including one or more public, private, or cloud networks, for example.

Each of the records server devices 14(1)-14(n) in this example includes one or more processors, a memory, and a communication interface, which are coupled together by a bus or other communication link, although other numbers and/or types of network devices could be used. The records server devices 14(1)-14(n) in this example process requests received from the electronic medical records computing apparatus 12 via the communication network(s) 18 according to the HTTP-based application RFC protocol, for example. Various applications may be operating on the records server devices 14(1)-14(n) and transmitting data (e.g., files or Web pages) to the medical client devices 16(1)-16(n) via the electronic medical records computing apparatus 12 in response to requests from the medical client devices 16(1)-16(n). The records server devices 14(1)-14(n)

may be hardware or software or may represent a system with multiple servers in a pool, which may include internal or external networks.

Although the records server devices **14(1)-14(*n*) are illustrated as single devices, one or more actions of each of the records server devices 14(1)-14(*n*) may be distributed across one or more distinct network computing devices that together comprise one or more of the records server devices 14(1)-14(*n*) for one or more different entities. Moreover, the records server devices 14(1)-14(*n*) are not limited to a particular configuration and may be associated with a variety of different entities. Thus, the records server devices 14(1)-14(*n*) may contain a plurality of network computing devices that operate using a master/slave approach, whereby one of the network computing devices of the records server devices 14(1)-14(*n*) operate to manage and/or otherwise coordinate operations of the other network computing devices. The records server devices 14(1)-14(*n*)** may operate as a plurality of network computing devices within a cluster architecture, a peer-to peer architecture, virtual machines, or within a cloud architecture, for example.

Thus, the technology disclosed herein is not to be construed as being limited to a single environment and other configurations and architectures are also envisaged. For example, one or more of the records server devices **14(1)-14(*n*) could operate within the electronic medical records computing apparatus 12, itself rather than as a stand-alone server device communicating with the electronic medical records computing apparatus 12** via the communication network(s).

The medical client devices **16(1)-16(*n*) in this example include any type of computing device, such as mobile computing devices, desktop computing devices, laptop computing devices, tablet computing devices, virtual machines (including cloud-based computers), or the like. Each of the medical client devices 16(1)-16(*n*)** in this example includes a processor, a memory, and a communication interface, which are coupled together by a bus or other communication link, although other numbers and/or types of network devices could be used.

The medical client devices **16(1)-16(*n*) may run interface applications, such as standard Web browsers or standalone client applications, which may provide an interface to make requests for and receive content, such as medical records, stored on one or more of the records server devices 14(1)-14(*n*) via the communication network(s) 18. The medical client devices 16(1)-16(*n*)** may further include a display device, such as a display screen or touchscreen, and/or an input device, such as a keyboard for example.

Although the exemplary electronic medical records computing apparatus 12, records server devices **14(1)-14(*n*), medical client devices 16(1)-16(*n*), and communication network(s) 18** are described and illustrated herein, other types and/or numbers of systems, devices, components, and/or elements in other topologies can be used. It is to be understood that the systems of the examples described herein are for exemplary purposes, as many variations of the specific hardware and software used to implement the examples are possible, as will be appreciated by those skilled in the relevant art(s).

One or more of the components depicted in the electronic medical records computing apparatus 12, records server devices **14(1)-14(*n*), or medical client devices 16(1)-16(*n*), for example, may be configured to operate as virtual instances on the same physical machine. In other words, one or more of the electronic medical records computing apparatus 12, records server devices 14(1)-14(*n*), or medical client devices 16(1)-16(*n*) may operate on the same physical device rather than as separate devices communicating through communication network(s). Additionally, there may be more or fewer of the electronic medical records computing apparatus 12, records server devices 14(1)-14(*n*), or medical client devices 16(1)-16(*n*) than illustrated in FIG. 1. The medical client devices 16(1)-16(*n*) could also be implemented as applications on the electronic medical records computing apparatus 12**, itself as a further example.

In addition, two or more computing systems or devices can be substituted for any one of the systems or devices in any example. Accordingly, principles and advantages of distributed processing, such as redundancy and replication also can be implemented, as desired, to increase the robustness and performance of the devices and systems of the examples. The examples may also be implemented on computer system(s) that extend across any suitable network using any suitable interface mechanisms and traffic technologies, including by way of example only teletraffic in any suitable form (e.g., voice and modem), wireless traffic networks, cellular traffic networks, Packet Data Networks (PDNs), the Internet, intranets, and combinations thereof.

The examples may also be embodied as one or more non-transitory computer readable media having instructions stored thereon for one or more aspects of the present technology as described and illustrated by way of the examples herein. The instructions in some examples include executable code that, when executed by one or more processors, cause the processors to carry out steps necessary to implement the methods of the examples of this technology that are described and illustrated herein.

An exemplary method for improving natural language processing with enhanced automated screening for automated generation of a clinical summarization report will now be described with reference to FIGS. 1-4. Referring more specifically to FIG. 3, in step 100 in this example the electronic medical records computing apparatus 12 may receive a request for patient medical records from one of the medical client devices **16(1)-16(*n*) for the generation of a clinical summarization record. Based on the received patient information and other information in the request, the electronic medical records computing apparatus 12 may generate and transmit one or more requests to one or more records server computing devices 14(1)-14(*n*) which may be associated with one or more different medical providers at other locations (for ease of illustration server computing devices 14(1)-14(*n*) have been shown). The one or more records server computing devices 14(1)-14(*n*) will process the requests and transmit one or more types of identified electronic medical records associated with the request back to the electronic medical records computing apparatus 12**. In this particular example, two types of electronic medical records are typically retrieved: Portable Document Format (PDF); and Consolidated Clinical Document Architecture (C-CDA), although other types and/or numbers of electronic medical records could be retrieved, such as Word or excel electronic medical records by way of example only.

In step 102, the electronic medical records computing apparatus 12 may process the one or more types of retrieved electronic medical records from the one or more records server computing devices **14(1)-14(*n*)** to convert each into a common electronic format. In this particular example, one type of retrieved electronic medical record is a PDF electronic medical record that may contain images that represent the content of the electronic medical record and/or may have textual content where the image representation of a character is a glyph. It is possible for the PDF electronic medical record(s) to have a "text layer" that maps the glyph to its character representation which can be constructed by the electronic medical records computing apparatus 12 using Optical Character Recognition (OCR) technology stored in memory 22 or other locations. Additionally, in this particular example another type of retrieved electronic medical record is a C-CDA electronic medical record which is an extensible markup language (XML) electronic medical record. C-CDA electronic medical records are used for a variety of reasons, such as for exchanging data about patients to administrative or patient population data exchange by way of example only. The retrieved C-CDA electronic medical records may be converted to a PDF format using a stylesheet transform and then passed through OCR by the electronic medical records computing apparatus 12 to reconstruct any textual information.

In step 104, the electronic medical records computing apparatus 12 may further split or otherwise segment or divide the converted electronic medical records based on visit type data and recorded visit date data, although the converted electronic medical records may be organized in other manners. In this particular example, the electronic medical records computing apparatus 12 may split the converted electronic medical records based on visit type data obtained from the converted electronic medical records into one or more sections and then may further organize the one or more converted electronic medical records in each section based on record visit date data obtained from the converted electronic medical records.

In step 106, the electronic medical records computing apparatus 12, may execute a natural language processing (NLP) algorithm 31 to obtain a subset of summarization data from each of the converted medical electronic records based on medical information data in the received request and/or one or more other factors, although other approaches for obtaining in this information can be used. By way of example, the electronic medical records computing apparatus 12, may execute a natural language processing (NLP) algorithm 31 to identify one or more terms in each of the converted medical electronic records that correspond to one or more stored terms, such as particular types of medical terms by way of example only. The electronic medical records computing apparatus 12 may further compare a stored weight of each identified term against a stored threshold and if above the threshold, then the electronic medical records computing apparatus 12 may select an adjustable stored number of sentences before and/or after the term for the summarization data, although other manners for obtaining the initial subset of data may be used.

By way of a further example, the electronic medical records computing apparatus 12, may execute a natural language processing (NLP) algorithm 31 to further screen the initial subset of summarization data based on one or more factors to generate a further reduced subset of summarization data for each of the converted medical electronic records. By way of example only, the one or more factors may comprise frequency of a term within the converted medical electronic record. If a term appears more than once, then the electronic medical records computing apparatus 12 executing the natural language processing (NLP) algorithm 31 may adjust the weight of the term based on a multiplier and that multiplier may vary based on the frequency of the appearance of the term, e.g. two appearances of a term may increase the weight by 5%, three appearances by 10%, etc, and then the adjusted weight of that term may be compared against the threshold as described above to determine when an adjustable stored number of sentences before and/or after the term are included in the summarization data.

By way of a further example, the electronic medical records computing apparatus 12, may execute a natural language processing (NLP) algorithm 31 to further screen the initial subset of summarization data based on the concurrence of two or more terms within each of the converted medical electronic records utilizing the concurrence database 29 within the converted medical electronic record, although other types and/or numbers of factors for enhanced screening may be used. If there is a concurrence of terms in the converted medical electronic record that match stored corresponding pairs of stored terms, then the electronic medical records computing apparatus 12 executing the natural language processing (NLP) algorithm 31 may adjust the weight of the identified terms with concurrence based on a stored multiplier and then the adjusted weight of those terms may be compared against the threshold as described above to determine when an adjustable stored number of sentences before and/or after the term are included in the summarization data. Additionally, multiple concurrences of the same pairs of terms may further be used by the electronic medical records computing apparatus 12 executing the natural language processing (NLP) algorithm 31 to adjust the weight of each of the terms, e.g. two concurrences of pairs of terms that correspond with stored matched terms may increase the weight by 5%, three concurrences by 10%, etc.

The natural language processing (NLP) algorithm 31 executed by the electronic medical records computing apparatus 12 also may be used to highlight one or more terms with the identified summarization data within each of the converted electronic medical records based on an identified with a set of stored terms in memory 22, such as the term "congestive heart failure" or other medical terms by way of example only, to alert a clinical professional at one of the medical client computing devices 16(1)-16n) with a prompt to allow an election and optional copying of this summarization data into the corresponding identified one of the plurality of templates based on their clinical judgement. By way of further example, the electronic medical records computing apparatus 12 may allow an operator to click on with the mouse button or otherwise select any term displayed during and/or following the execution of the NLP algorithm 31 to update the weight in the term weights database 30, such as a term related to a current disease state, thus increasing or decreasing the selected term's relative importance for the current or future enhanced screenings by the NLP algorithm 31 The electronic medical records computing apparatus 12 may store the obtained summarization data in the memory 22 for generation of the clinical summarization record, although the information could be stored in other locations or be utilized in real time.

In step 108, the electronic medical records computing apparatus 12 identifies one of a plurality of templates from template database 28, such as a radiology template or a pathology template by way of example only for each of the converted electronic medical records based on one or more factors, such as an institution associated with the received request, a department associated with the received request, or a disease type associated with the received request by way of example only. By way of further example, subtypes may be used by the electronic medical records computing apparatus 12 to provide an indication of further refinement; for example, a radiology document may have the subtypes of Magnetic Resonance Imaging (MRI), Computed Tomography (CT). Each of the identified ones of the plurality of templates in the template database 28 may be used to collect data and metadata including on a document type and subtype for each of the converted electronic medical records. By way of example only, other optional data that may be collected by the electronic medical records computing apparatus 12 may include data about the diagnosis, a microscopic description, results, interpretation, body part, lab values, etc. The electronic medical records computing apparatus 12 may populate at least a portion of the obtained reduced subset of summarization data that is then populated into a plurality of data fields within one of a plurality of templates identified for each of the converted electronic medical records from the reduced subset of summarization data for each of the converted medical electronic records.

In step 110, the electronic medical records computing apparatus 12 retrieves the obtained summarization data in each of the identified ones of the plurality of templates from memory 22 in this example and generates a clinical summarization report. In this particular example, the electronic medical records computing apparatus 12 selects one of a plurality of clinical report formats from the clinical reports format database 32 based on an institution and disease type associated with the received request from one of the medical client devices 16(1)-16(n), although the clinical report format can be selected in other manners based on other types and/or numbers of factors. Next, the electronic medical records computing apparatus 12 populates the selected one of the plurality of clinical report formats with the obtained data in each of the identified ones of the plurality of templates, although the selected one of the plurality of clinical report formats may be generated in other manners. Additionally, the electronic medical records computing apparatus 12 may further populate the selected one of the plurality of clinical report formats with other obtained data from the initial request and/or other sources, such as with the patient name, date of birth, and medical record number, as well as a listing of the primary diagnosis. Further, the electronic medical records computing apparatus 12 may organize the data in the selected one of the plurality of clinical report formats with the most relevant information, such as radiology and pathology reports first by way of example. The electronic medical records computing apparatus 12 in the selected one of the plurality of clinical report formats may also generate two or more summarizations, such as an extractive and indicative summarization and an abstract clinical summarization, based on the obtained data, although other types and/or numbers of summarization may be generated. An example of a generated clinical summarization report is illustrated in FIG. 4.

In step 112, the electronic medical records computing apparatus 12 may generate an overall indexed document based on the one or more sections with the generated clinical summarization. In this particular example, each of the retrieved one or more electronic medical records may be arranged by the identified sections and then may be organized within each section in reverse chronological order to form the overall indexed document by the electronics medical record computing apparatus 12. The electronic medical records computing apparatus 12 may also further generate a cover page containing a patient's demographics, diagnosis and hyperlinks to each section or section in the overall indexed document from the generated clinical summarization report, although other types and/or amounts of data and other links may be used. Further, the electronic medical records computing apparatus 12 may generate a table of contents that may be used to provide an indication of a location of key terms within the file. By way of example only, the electronic medical records computing apparatus 12 may link terms that correspond with a stored set of terms in memory 22, such as the term "carcinoma" into a table of contents that, when selected, would take the requesting one of the medical client devices 16(1)-16(n) to the appropriate page(s) in the overall indexed document with all instances of the term "carcinoma" highlighted for easy reference. The electronic medical records computing apparatus 12 may also add barcodes into the generated clinical summarization record indicating the patient name, medical record number, date of birth, and/or document type for easier identification.

In step 114, the electronic medical records computing apparatus 12 may deliver the overall indexed document with the generated clinical summarization record to the one of the medical client devices 16(1)-16(n) that made the initial request using Health Level 7 (HL7), although the overall indexed document with the generated clinical summarization record may be provide in other manners and/or may be stored for future use.

Accordingly, as illustrated and described by way of the examples herein, this technology provides methods, non-transitory computer readable media, and devices for improving natural language processing with enhanced automated screening for automated generation of a clinical summarization report. This technology achieves a higher level of accuracy through the use of a natural language processing (NLP) algorithm that obtains key concepts and provides guidance on what should be included in the clinical summarization report, thus substantially reducing the possibility of overlooking important retrieved data that may be contained with pages of record data and further increasing efficiency. Additionally, examples of this technology provide substantially more accurate clinical summarization reports through the use of an automated template-based system that is specific to an institution, department and/or disease type.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A method for improving natural language processing with screening for automated generation of a clinical summarization report implemented by a clinical summary management computing system comprising one or more clinical summary management computing apparatuses, client devices, or server devices, the method comprising:

converting into a common electronic format a plurality of different types of electronic medical records retrieved in response to a received request with patient identification data;

applying a natural language processing algorithm to obtain an initial subset of summarization data from each of the converted medical electronic record based on medical information data in the received request and then further screen with the natural language processing algorithm the initial subset of summarization data based on one or more stored factors to generate a reduced subset of summarization data for each of the converted medical electronic records, wherein the further screen comprises comparing a weight that is adjustable based on a frequency of each identified term in the initial subset of summarization data against a threshold and when above the threshold selecting one or more sentences at least one of before or after each identified term above the threshold for the reduced subset of summarization data;

populating at least a portion of the reduced subset of summarization data into a plurality of data fields within at least one of a plurality of templates identified for the converted electronic medical records;

generating a clinical summarization record based on the at least a portion of the reduced subset of summarization data populated in the at least one of the plurality of templates; and providing the clinical summarization record in response to the received request.

2. The method as set forth in claim 1 wherein the one or more factors comprise frequency of a term, concurrence of terms, and stored weight of a term in the subset of data, wherein the natural language processing algorithm removes one or more terms from the subset of data which occur at a rate below a stored threshold frequency, adds one or more terms from the subset of data with an identified concurrence based on a stored concurrence relationship, and removes one or more terms from the subset of data with a stored weight below a stored threshold weight.

3. The method as set forth in claim 1 further comprising separating the converted electronic medical records data based on type of visit data into one or more sections and organizing the converted electronic medical records in each of the one or more sections based on the recorded visit date data obtained from each of the converted electronic medical records.

4. The method as set forth in claim 3 further comprising:
generating an overall indexed document of the retrieved electronic medical records based on the one or more sections with the generated clinical summarization with one or more hyperlinks from at least a portion of the reduced subset of summarization data in the generated clinical summarization to a corresponding source of the at least a portion of the reduced subset of summarization data in the overall indexed document; and providing the generated overall indexed document in a response to the received request.

5. The method of claim 4, wherein the generating the overall indexed document further comprises organizing each of the retrieved one or more electronic medical records within each of the one or more sections in reverse chronological order.

6. The method of claim 1, wherein the one or more factors for the identifying one of a plurality of templates for each of the converted electronic medical records comprise an institution associated with the received request, a department associated with the received request, one or more diagnosis codes associated with the retrieved request or in the converted electronic medical record, or a disease type identified in the converted electronic medical records.

7. The method of claim 1, wherein the generating a clinical summarization record further comprises generating at least two different types of summaries comprising a combined extractive and indicative summarization and an abstract clinical summarization.

8. An electronic medical records computing apparatus, comprising memory comprising programmed instructions stored thereon and one or more processors configured to be capable of executing the stored programmed instructions to:

convert into a common electronic format a plurality of different types of electronic medical records retrieved in response to a received request with patient identification data;

apply a natural language processing algorithm to obtain an initial subset of summarization data from each of the converted medical electronic record based on medical information data in the received request and then further screen with the natural language processing algorithm the initial subset of summarization data based on one or more stored factors to generate a reduced subset of summarization data for each of the converted medical electronic records, wherein the further screen comprises comparing a weight that is adjustable based on a frequency of each identified term in the initial subset of summarization data against a threshold and when above the threshold selecting one or more sentences at least one of before or after each identified term above the threshold for the reduced subset of summarization data;

populate at least a portion of the reduced subset of summarization data into a plurality of data fields within at least one of a plurality of templates identified for the converted electronic medical records;

generate a clinical summarization record based on the at least a portion of the reduced subset of summarization data populated in the at least one of the plurality of templates; and provide the clinical summarization record in response to the received request.

9. The apparatus as set forth in claim 8 wherein the one or more factors comprise frequency of a term, concurrence of terms, and stored weight of a term in the subset of data, wherein the natural language processing algorithm removes one or more terms from the subset of data which occur at a rate below a stored threshold frequency, adds one or more terms from the subset of data with an identified concurrence based on a stored concurrence relationship, and removes one or more terms from the subset of data with a stored weight below a stored threshold weight.

10. The apparatus as set forth in claim 8 wherein the one or more processors are further configured to be capable of executing the stored programmed instructions to separate the converted electronic medical records data based on type of visit data into one or more sections and organizing the converted electronic medical records in each of the one or more sections based on the recorded visit date data obtained from each of the converted electronic medical records.

11. The apparatus as set forth in claim 10 wherein the one or more processors are further configured to be capable of executing the stored programmed instructions to:

generate an overall indexed document of the retrieved electronic medical records based on the one or more sections with the generated clinical summarization with one or more hyperlinks from at least a portion of the reduced subset of summarization data in the generated clinical summarization to a corresponding source of the at least a portion of the reduced subset of summarization data in the overall indexed document; and provide the generated overall indexed document in a response to the received request.

12. The apparatus of claim 11, wherein the generate the overall indexed document further comprises organizing each of the retrieved one or more electronic medical records within each of the one or more sections in reverse chronological order.

13. The apparatus of claim 8, wherein the one or more factors for the identifying one of a plurality of templates for each of the converted electronic medical records comprise an institution associated with the received request, a department associated with the received request, one or more diagnosis codes associated with the retrieved request or in the converted electronic medical record, or a disease type identified in the converted electronic medical records.

14. The apparatus of claim 8, wherein the generate a clinical summarization record further comprises generate at least two different types of summaries comprising a combined extractive and indicative summarization and an abstract clinical summarization.

15. A non-transitory computer readable medium having stored thereon instructions improving natural language processing with enhanced automated screening for automated generation of a clinical summarization report comprising executable code which when executed by one or more processors, causes the one or more processors to:
   convert into a common electronic format a plurality of different types of electronic medical records retrieved in response to a received request with patient identification data;
   apply a natural language processing algorithm to obtain an initial subset of summarization data from each of the converted medical electronic record based on medical information data in the received request and then further screen with the natural language processing algorithm the initial subset of summarization data based on one or more stored factors to generate a reduced subset of summarization data for each of the converted medical electronic records, wherein the further screen comprises comparing a weight that is adjustable based on a frequency of each identified term in the initial subset of summarization data against a threshold and when above the threshold selecting one or more sentences at least one of before or after each identified term above the threshold for the reduced subset of summarization data;
   populate at least a portion of the reduced subset of summarization data into a plurality of data fields within at least one of a plurality of templates identified for each of the converted electronic medical records;
   generate a clinical summarization record based on the at least a portion of the reduced subset of summarization data populated in the at least one of the plurality of templates; and
   provide the clinical summarization record in response to the received request.

16. The medium as set forth in claim 15 wherein the one or more factors comprise frequency of a term, concurrence of terms, and stored weight of a term in the subset of data, wherein the natural language processing algorithm removes one or more terms from the subset of data which occur at a rate below a stored threshold frequency, adds one or more terms from the subset of data with an identified concurrence based on a stored concurrence relationship, and removes one or more terms from the subset of data with a stored weight below a stored threshold weight.

17. The medium as set forth in claim 15 wherein the executable code when executed by the one or more processors further causes the one or more processors to:
   separate the converted electronic medical records data based on type of visit data into one or more sections and organizing the converted electronic medical records in each of the one or more sections based on the recorded visit date data obtained from each of the converted electronic medical records.

18. The medium as set forth in claim 17 wherein the executable code when executed by the one or more processors further causes the one or more processors to:
   generate an overall indexed document of the retrieved electronic medical records based on the one or more sections with the generated clinical summarization with one or more hyperlinks from at least a portion of the reduced subset of summarization data in the generated clinical summarization to a corresponding source of the at least a portion of the reduced subset of summarization data in the overall indexed document; and
   provide the generated overall indexed document in a response to the received request.

19. The medium of claim 18, wherein the generate the overall indexed document further comprises organizing each of the retrieved one or more electronic medical records within each of the one or more sections in reverse chronological order.

20. The medium of claim 15, wherein the one or more factors for the identifying one of a plurality of templates for each of the converted electronic medical records comprise an institution associated with the received request, a department associated with the received request, one or more diagnosis codes associated with the retrieved request or in the converted electronic medical record, or a disease type identified in the converted electronic medical records.

21. The medium of claim 11, wherein the generate a clinical summarization record further comprises generate at least two different types of summaries comprising a combined extractive and indicative summarization and an abstract clinical summarization.

* * * * *